(12) United States Patent
Paz

(10) Patent No.: US 11,819,547 B2
(45) Date of Patent: Nov. 21, 2023

(54) VIRUS VACCINATION SYSTEM AND METHODS

(71) Applicant: Albert Paz, Apex, NC (US)

(72) Inventor: Albert Paz, Apex, NC (US)

( * ) Notice: Subject to any disclaimer, the term of this patent is extended or adjusted under 35 U.S.C. 154(b) by 372 days.

(21) Appl. No.: 17/108,004

(22) Filed: Dec. 1, 2020

(65) Prior Publication Data

US 2021/0290751 A1    Sep. 23, 2021

Related U.S. Application Data

(60) Provisional application No. 62/993,358, filed on Mar. 23, 2020.

(51) Int. Cl.
| | | |
|---|---|---|
| *A61K 39/12* | (2006.01) | |
| *A61M 16/06* | (2006.01) | |
| *A61M 16/08* | (2006.01) | |
| *A61M 16/10* | (2006.01) | |
| *A61K 39/00* | (2006.01) | |

(52) U.S. Cl.
CPC ............ *A61K 39/12* (2013.01); *A61M 16/06* (2013.01); *A61M 16/0875* (2013.01); *A61M 16/10* (2013.01); *A61K 2039/5252* (2013.01); *A61K 2039/544* (2013.01); *A61M 2202/30* (2013.01); *A61M 2205/3306* (2013.01); *A61M 2205/3368* (2013.01); *A61M 2205/583* (2013.01); *A61M 2209/084* (2013.01)

(58) Field of Classification Search
CPC ... A61K 39/12; A61M 16/10; A61M 16/0875; A61M 16/06
See application file for complete search history.

(56) References Cited

U.S. PATENT DOCUMENTS

| | | | | |
|---|---|---|---|---|
| 3,307,835 | A * | 3/1967 | Perlman .................... | F24F 6/04 261/96 |
| 4,750,643 | A * | 6/1988 | Wortrich ................. | A61M 5/14 604/173 |
| 2007/0199566 | A1* | 8/2007 | Be'eri ................. | A61M 16/024 128/204.23 |
| 2015/0048530 | A1* | 2/2015 | Cheung ............. | A61M 16/0883 261/135 |
| 2018/0168484 | A1* | 6/2018 | Rahamim ............ | A61B 5/7278 |
| 2019/0201650 | A1* | 7/2019 | McCracken ...... | A61M 16/1075 |

FOREIGN PATENT DOCUMENTS

CN        202040926 U  * 11/2011

* cited by examiner

*Primary Examiner* — Samchuan C Yao
*Assistant Examiner* — Tina Zhang
(74) *Attorney, Agent, or Firm* — Lambert Shortell & Connaughton; David J. Connaughton, Jr.; Justin P. Tinger

(57) ABSTRACT

A vaccine formation and delivery system includes a first chamber configured to store a live virus and a second chamber for storing an inactivated virus. The system further includes a UV radiation means used for irradiating the live virus. Personal dosage transfer chambers and a delivery system configured to attach to the personal dosage transfer chambers for delivering an inactive virus to a user.

11 Claims, 3 Drawing Sheets

VIRUS VACCINATION SYSTEM AND METHODS

This application claims priority from U.S. Provisional Appl. No. 62/993,358, filed on Mar. 23, 2020, the contents of which are incorporated herein in their entirety.

FIELD OF THE INVENTION

The present invention relates generally to systems and methods used to create and deliver vaccines.

BACKGROUND OF THE INVENTION

Several types of vaccines exist and are created using different methodologies. These include live-attenuated, inactivated/killed, Toxoid (inactivated toxin), subunit, and conjugate vaccines. Live-attenuated vaccines use a weakened form of the virus that causes a disease to assist in building immunity. Often one or two doses of most live-attenuated vaccines can give a lifetime of protection. Inactivated or killed vaccines usually involve taking a dead virus or parts of a dead virus to create a vaccine. These have the advantage of not getting a person sick. For example, Polio in the United States used to use a live-attenuated vaccine and switched to inactivated version because even with the live-attenuated version a few people would contract polio from the vaccine itself each year. Toxoid vaccines involve chemically inactivating the bacteria that create harmful toxins. Subunit and conjugate vaccines use only parts of the virus to try and provoke an immune response.

In the present day, annually the flu, SARS, and currently COVID-19 arise, which each are able to mutate and generate different strands of the virus. This is why a new flu vaccine is developed each year to try and reduce the spread the flu. This development and deployment process can take a while to create. In the current case of COVID-19 no vaccine has been developed after about a year of the virus becoming known and rapidly spreading.

The present application seeks to provide a system and method for deploying a faster response to annual viruses that appear to mutate each year.

SUMMARY OF THE INVENTION

Accordingly, in one embodiment a system for creating a breathable vaccine is comprised of a first chamber that is configured for housing a live virus. In some variations the first chamber is configured to be mobile, while in other variations it is a fixed within a safety room or another safety chamber. The system further comprises a second chamber that is configured for receiving the live virus from the first chamber via a transfer mechanism. The second chamber can include one or more UV sources configured for irradiating the live virus received therein for a period of time, whereby the irradiating process forms an inactivated virus that forms the basis for the vaccine. Connected to the second chamber include one or more personal dosage chambers wherein a portion or individual dosage amount can be transferred into from the second chamber. Each of the personal dosage chambers are configured to be connected to a delivery tube that allows the breathable vaccine to transfer from the personal dosage chamber into an inhaler mask, wherein a user can utilize to inhale the breathable vaccine into their body. The breathable vaccine formed of the inactivated virus components can then work inside the user's body to generate an amount of inoculation against the live virus.

In some variations of the above embodiment, the second chamber is configured to be mobile, which can include being configured to be transported by another device, such as dolly or transfer cart. It can also have attaching wheels or tracks to the second chamber to allow it to roll or glide. Advantages of having a movable or transportable second chamber include being able to have the live virus centrally located in a few strategic and well-managed facilities, while the second chambers can be transported easily to a plurality of locations where the breathable vaccine can be delivered to a plurality of users.

In another variant of the embodiment above, some of the plurality of dosage chambers can include a viewing window. This viewing window can be used in conjunction with a sensor or other testing equipment such as microscopes, ozone meters, radiometers, pressure sensors, and temperature sensors.

As noted, the system for creating a breathable vaccine above can further include a safety chamber where the first and second chamber are stored. In other versions of the system above, the first chamber can be stored in a safety room. The safety chamber and the safety room can be configured to have redundant UV sources and configured to detect leakage from the first and second chambers. The most critical being wherever the live virus is being stored. An inactivated virus is less susceptible to cause harm.

The first or second chambers, depending on the embodiment, can include UV sources, that irradiate the live virus stored therein.

The live virus and later inactivated virus or breathable vaccine can be transferred between chambers using a transfer mechanism that has one or more valves disposed therein. The transfer can be aided by creating a higher pressure in one chamber versus the receiving chamber. In one embodiment, the first chamber is positively pressurized prior to transferring the live virus into the second chamber.

In another embodiment, the second chamber is negatively pressurized prior to receiving the live virus, so that it sucks or vacuums the live virus (or inactivated virus) into the second chamber.

As noted above the second chamber is detachable from the first chamber so that it can easily transported to various locations.

When irradiating the live virus in the first or second chamber, the first or second chamber can include an air circulating device, such as a fan, a tumbler, jet nozzles, or any other device configured to circulate or stir up the air inside the chamber. This can aide in ensuring that all of the live virus is properly irradiated.

Methods for creating and delivering a breathable vaccine comprise the steps of growing the live virus in a first chamber that is configured for housing the live virus. Transferring the live virus via a transfer mechanism into a second chamber and irradiating the live virus for a specified period of time. The time can be determined in part on the geometry and size of the second chamber. Once the live virus is inactivated it can used to form at least part of the breathable vaccine.

The breathable vaccine can be transferred into dosage portions from the second chamber into a plurality of dosage chambers. A delivery tube can connect the personal dosage chamber to an inhaler mask and facilitate the transfer of breathable vaccine from the personal dosage chamber to the inhaler mask where the user can then inhale the breathable vaccine into their body.

The method can further include the step of detaching the second chamber from the first chamber and transporting the second chamber to a site configured to deliver the breathable vaccine prior to delivering the breathable vaccine to individual users.

One or more of the personal dosage chambers containing a portion of the breathable vaccine can be tested to ensure safety and viability.

The safety testing can include testing for levels of ozone in the breathable vaccine. The safety testing can also include testing for levels of live virus.

It should be understood that multiple second chambers can used with a single first chamber. It should also be understood that each of the chambers can be pressurized to enable the transfer between chambers and ultimately to the inhaler mask.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

This application describes multiple embodiments of a vaccine formation and delivery system as well as methods of generating and delivering a vaccine using the various vaccine formation and delivery systems described herein.

Terms including chamber or container are meant to describe vessels with sidewalls having a volume disposed therein. The term UV irradiation is meant to convey the ultra-violet range of the electromagnetic spectrum that is useful for killing or inactivating viruses. It should be understood that alternative wavelengths on the electromagnetic spectrum that can kill or inactivate viruses can also be utilized with the embodiments described herein.

The primary embodiments described herein focus on using whole-virus vaccines that are inactivated or killed using radiation and/or heat. The parts of the virus that are allowed to grow and mutate are destroyed using radiation and heat, while the remaining components are left behind that form an antigen, which can be deployed into the body for which the body can create a new antibody for. Multiple doses of an inactivated vaccine may be required for the body to build up an appropriate immunity against the live virus.

Figure 1:
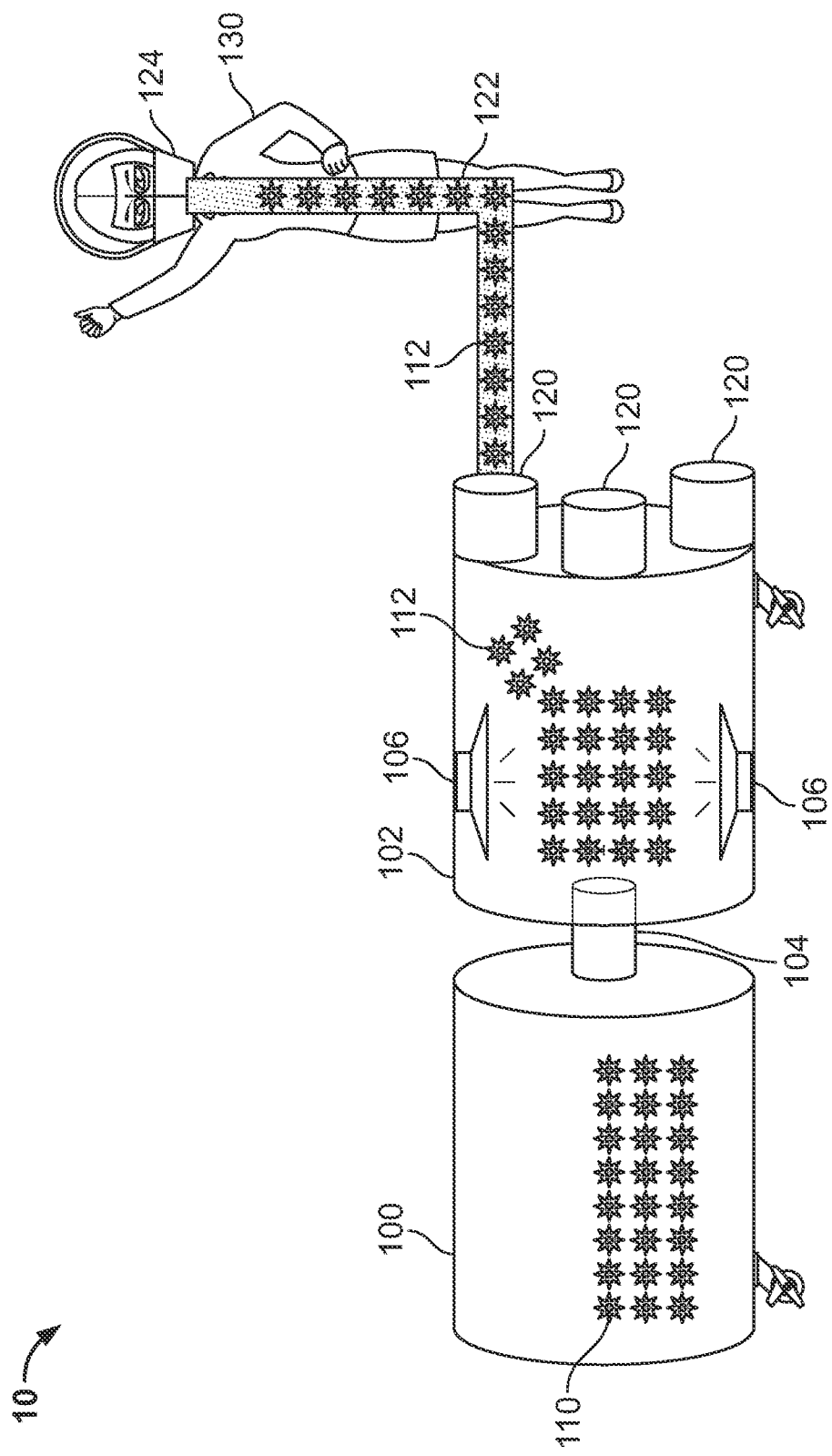
FIG. 1 illustrates an exemplary schematic of a vaccine formation and delivery system.

FIG. 1 illustrates a system 10 for creating and delivering inactivated viruses. Chamber 100 has a volume therein and is configured to contain a cultivated sample of a live virus 110, such as the COVID-19 virus or another respiratory virus. Chamber 100 can foster a growth-rich environment, which can include nutrients for the virus to replicate, ideal temperatures, and gas mixtures to maintain a viable supply. Chamber 100 is configured to be transportable, as shown with wheels in the present embodiment, and is a hermetically sealed chamber. A transfer mechanism 104 can be connected with chamber 100 and opposite with chamber 102. The transfer mechanism 104, can include hermetically sealable valves and control pressure between chambers 100 and 102. Pneumatic or hydraulic pistons in chamber 100 can pressurize and force the live virus content to be transferred via the transfer mechanism 104 to chamber 102 at a specific pressure measured by a pressure gauge. Alternatively, chamber 102 can have a negative pressure associated with it, wherein opening the transfer mechanism passageway between the two chambers can cause chamber 102 to vacuum in live virus from chamber 100.

Chamber 102 is also hermetically sealed and configured to receive the live virus 110 from Chamber 100. Upon receiving a particular amount of live virus 100, UV radiation sources 106 include UV LEDs, UV lights, and other UV producing devices, can be activated for a designated period of time to irradiate the live virus 110 and convert it to an inactivated virus 112. Internal tumblers (not shown), fans and other internal mixing mechanisms can be utilized to stir the live virus 110 about while it is being irradiated by the UV sources 106.

Individual dosage chambers 120 can further draw in or alternatively have forced therein an amount equal to a personal dosage. The dosage chamber can be connected to a delivery tube 122, which transfers the inactivated virus dosage via an inhaler mask 124 into the user 130, where the body can begin creating antibodies.

In some configurations, one of the individual dosage chambers can be a testing chamber for determining that the virus content has been completely inactivated. This personal dosage chamber 120 can be detachable and taken to a lab where an analysis can be performed. Upon successfully confirming the virus has become inactivated 112, multiple dosages can be administered to individuals 130. It should be understood that that various components of the system can be designed to be disposable, such as the inhaler mask and delivery tube 122. The rate about which the user 130 can inhale the gaseous vaccine containing the inactivated virus 112 can be modified. Some methods including modifying the pressure output of the personal dosage container 120.

Testing equipment such as microscopes, ozone meters, temperature sensors, radiometers, light sensors, and so forth can attached to or used in conjunction with the personal dosage containers for determining viability and safety.

Some of the advantages of the systems and methods already described herein, include utilizing century old techniques of administering inactivated viruses to individuals in order to create immunity to new viruses. In the instance of the current Covid-19 pandemic, multiple systems could be deployed in a rapid fashion, where users can receive immunity building inactivated viruses. This type of system can be deployed quickly as opposed to waiting for long periods of time for other types of vaccines to be created.

Figure 2:
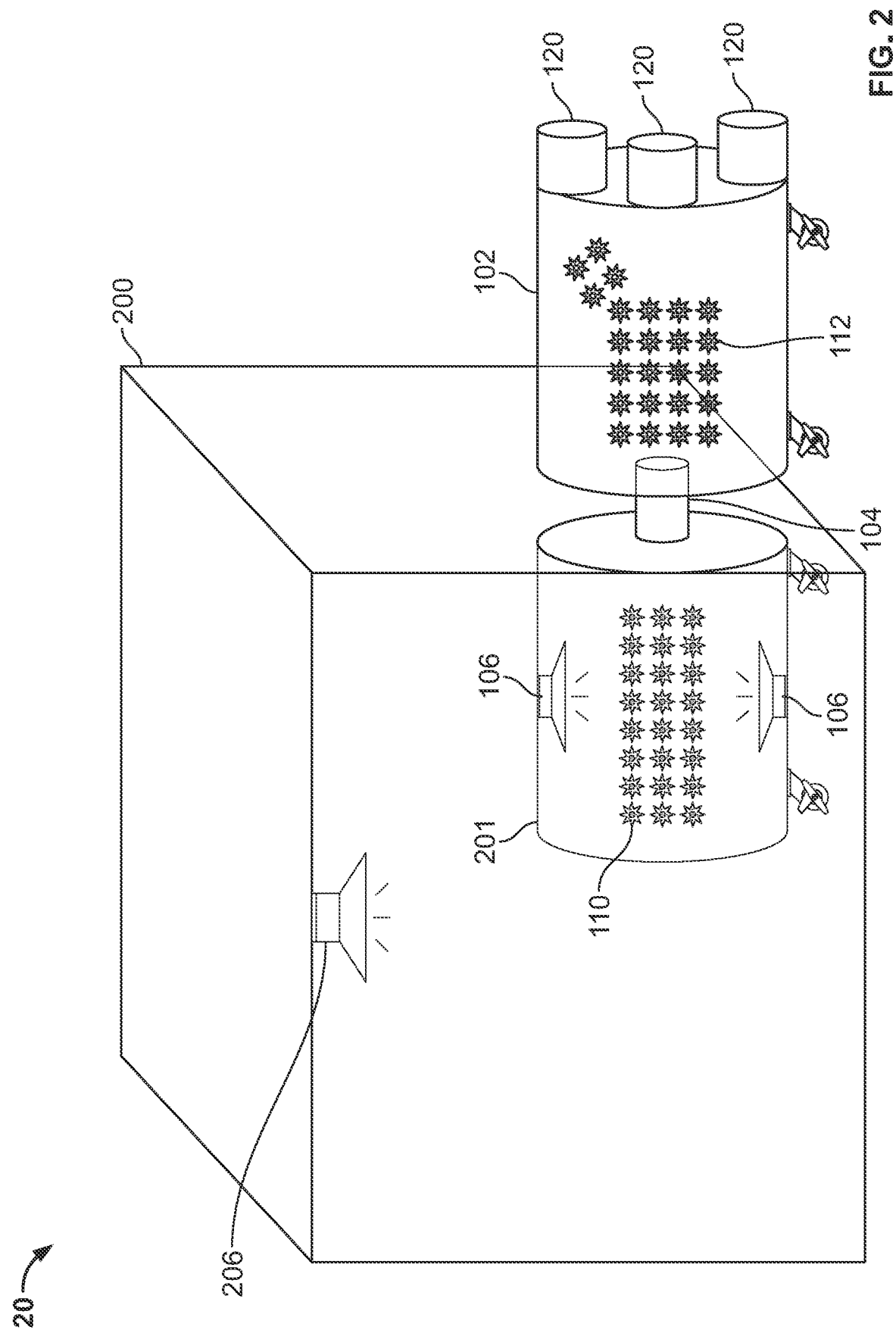
FIG. 2 illustrates an exemplary schematic of a vaccine formation and delivery system with additional safety features.

FIG. 2 illustrates another embodiment of a vaccine creating system 20, including a chamber 201 used for storing live virus and irradiated the live virus using UV sources 106. The chamber 201 is disposed in a room 200, which has redundant UV sources 206 that are periodically activated to ensure that in the event of any leakage of the live virus, the room can be irradiated and sanitized. A transfer mechanism 104 can be used to transfer inactivated virus 112 into chamber 102, which can then be moved to a location where personal doses can be administered to users 130 via the personal dosage containers 120, via the transfer tube 122 into the inhaler mask 124. As shown chamber 102 includes wheel for moving the chamber about. It can also be realized that someone skilled in the art can utilize other transfer carts or dollies to move chamber 102 about.

It should be noted that chamber 201 can also simply be an irradiating chamber and the live virus can be grown or cultivated in room 200. Once the virus is inactivated, chamber 102 can be transported to multiple places without risk of harm, as the virus has already been inactivated. In some instances, to prevent further degradation of the inactivated virus, the chambers can include temperature controls to maintain at a certain temperature until the doses can be delivered.

Figure 3:
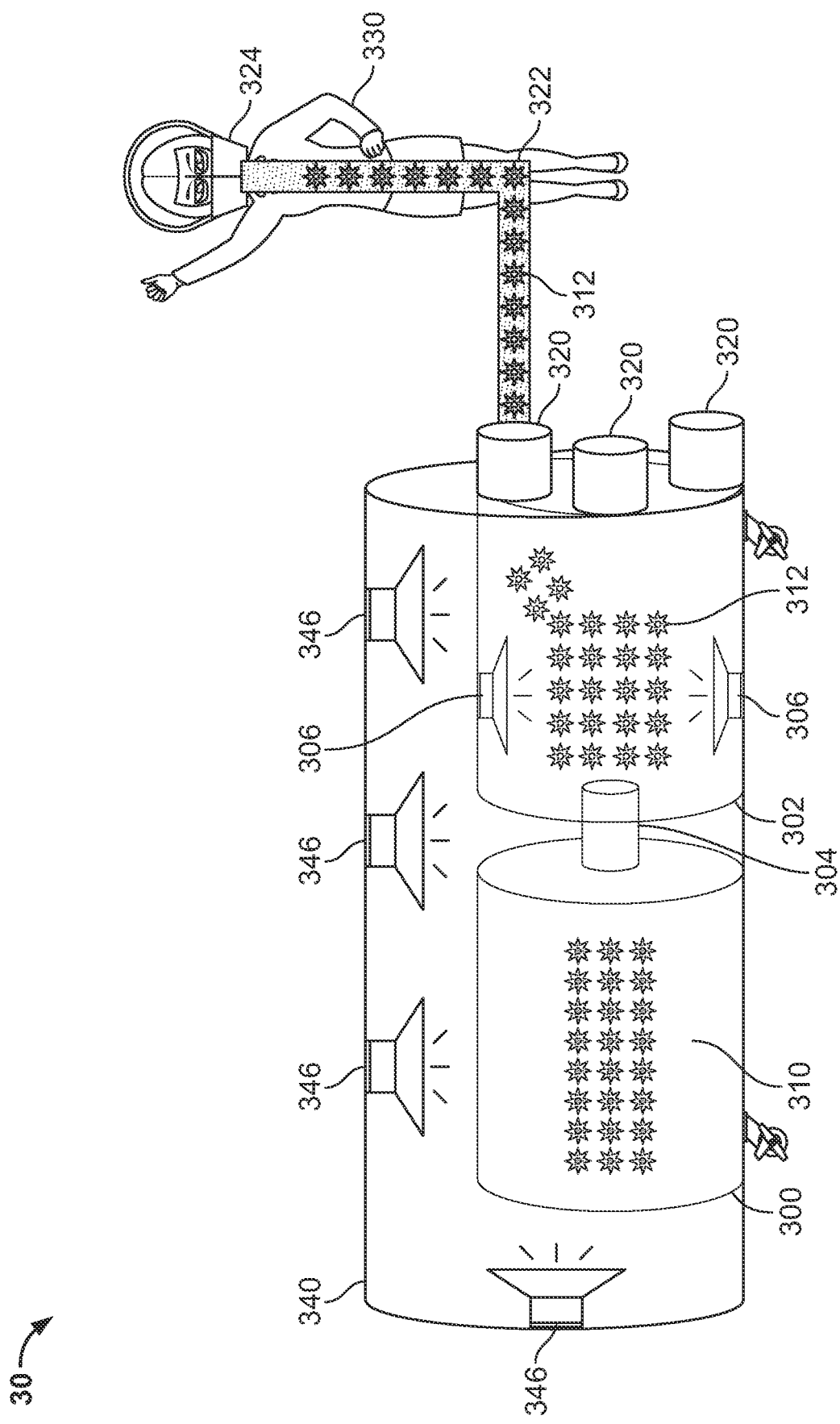
FIG. 3 illustrates yet another exemplary schematic of a vaccine formation and delivery system with yet additional safety features.

FIG. 3 illustrates yet another embodiment where the live virus 310 is cultivated in chamber 300, which is stored inside of safety chamber 340. A transfer mechanism 304 is disposed between chamber 300 to chamber 302, where the live virus is irradiated and turned into an inactivated virus 312 used as a vaccine to be delivered via the personal dosage chambers 320 into the delivery tube 322 into the inhaler mask 324 where the user 330 inhales or breathes the vaccine into their system. Chamber 302 contains UV sources 306 used to irradiate the live virus 310. Redundant or backup UV sources 346 are positioned in safety chamber 340 in case of a leak from chamber 302 or 304 before complete irradiation has occurred.

Transfer mechanisms 104, 304 can include various types of valves including one-way valves, pressure valves, single-use valves, and so forth. They can be formed of a unibody housing or include tubing configured to handle various pressures, including higher pressures from one chamber to the next chamber. In some variants a UV radiation source can be secured within the transfer mechanism to irradiate before and after a transfer from one chamber to another chamber as an additional redundant safety feature. The attachment ends can include various couplings, press or screw-on known in the art.

It should be understood that once a transfer has occurred from one chamber to another that the transfer mechanism and valves are then closed. Each chamber can have one or more valves associated therewith.

The personal dosage chambers are configured to deliver enough of a viral payload (of inactivated whole virus) to allow the users to create an immunity to the live virus. As noted, these dosage amounts can be controlled by the amount of pressure allowed into the personal dosage container. The inactivated virus can be delivered with normal air, air having an increase in oxygen levels, or other mixture levels that aid in the delivery process. The personal dosage chambers can also include viewing windows whereby a microscope, ozone meter, radiometer and other sensors can be affixed thereto. These pieces of equipment can be used to test or verify the viral payload, safety, amount of inactivated vs. live virus, ozone levels, and other features. In the event ozone or some other undesirable gas is detected, a reagent may be added to the chamber to reduce or eliminate any ozone formed therein. Some of these include non-harmful bacterium and carbon monoxide, as well as additional live virus. Sometimes UV radiation sources and in particular ranges such as between 160 nm-240 nm can react with oxygen to form ozone. In some embodiments, when irradiating the live virus, an additional gas, such as nitrogen can be added to reduce the amount of ozone generation. Alternatively, modifying the UV radiation wavelengths can help reduce potential ozone creation.

The amount and time of UV irradiation can primarily be determined based on the geometry and size of the chamber. It can also be determined in part by the specific UV wavelength that is being utilized.

In one arrangement, the UV sources can be replaced along the external wall of the chambers, where they are partially disposed within the chamber, but where a hermetically sealed transparent aperture or window is formed to allow for the UV sources to be changed without risk of depressurizing or having to open up the chamber.

Again, some of the advantages of the systems and methods described herein include utilizing the live virus in a known region to treat users in that region with an inactivated version. As opposed to creating a vaccine that is used in multiple regions, which may or may not be effective against all of the various strains that might exist. It is understood that a new flu vaccine is created each year, because of such mutations and variations.

Another advantage noted above is rapid deployment by utilizing chambers that are transportable to various facilities for delivering the formed vaccine. On the spot vaccine generating, which reduces the degradation for transporting over long distances. In other words, the live virus can be converted to an inactivated version in minutes and ready for deploying minutes thereafter. This type of system can be used with a variety of viruses including: Ebola, Whooping Cough, Influenza, Tuberculosis, and so forth. In some configurations, treated samples may be extracted from the system 10, 20, or 30 and suspended in an aqueous solution for delivery via an injection if preferred.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

The invention claimed is:

1. A system for creating a breathable vaccine comprising:
    a first chamber configured for housing a live virus;
    a second chamber configured for receiving the live virus from the first chamber via a transfer mechanism, the second chamber having one or more UV sources configured for irradiating the live virus received therein for a period of time, thus forming an inactivated virus forming a vaccine;
    a plurality of dosage chambers, configured to receive an amount of the vaccine generated by the second chamber;
    a delivery tube for attaching to one of the dosage chambers;
    an inhaler mask that is configured to be worn by a user for purposes of inhaling the vaccine from the dosage container through the delivery tube into the inhaler mask; and
    a safety chamber wherein the first and second chamber are stored therein, wherein the safety chamber includes a plurality of redundant UV sources.

2. The system for creating a breathable vaccine of claim 1, wherein the first or second chamber is mobile.

3. The system for creating a breathable vaccine of claim 2, wherein the second chamber has a plurality of wheels.

4. The system for creating a breathable vaccine of claim 1, wherein one of the plurality of dosage chambers has a viewing window.

5. The system for creating a breathable vaccine of claim 4, further including sensor equipment configured to test the formed vaccine stored in one of the plurality of dosage chambers.

6. The system for creating a breathable vaccine of claim 5, wherein the sensor equipment consists of at least one of the following: microscope, radiometer, ozone meter, and temperature sensor.

7. The system for creating a breathable vaccine of claim 1, wherein the first chamber is positively pressurized.

8. The system for creating a breathable vaccine of claim 1, wherein the second chamber is negatively pressurized.

9. The system for creating a breathable vaccine of claim 1, wherein the second chamber is detachable from the first chamber and transportable.

10. The system for creating a breathable vaccine of claim 1, wherein the second chamber further includes an air circulating device.

11. A system for creating a breathable vaccine comprising:
- a first chamber configured for housing a live virus;
- a second chamber configured for receiving the live virus from the first chamber via a transfer mechanism, the second chamber having one or more UV sources configured for irradiating the live virus received therein for a period of time, thus forming an inactivated virus forming a vaccine;
- a plurality of dosage chambers, configured to receive an amount of the vaccine generated by the second chamber;
- a delivery tube for attaching to one of the dosage chambers;
- an inhaler mask that is configured to be worn by a user for purposes of inhaling the vaccine from the dosage container through the delivery tube into the inhaler mask; and
- a safety room having a plurality of redundant UV sources disposed therein, and wherein the first chamber is stored therein.

\* \* \* \* \*